United States Patent [19]

Meyer et al.

[11] Patent Number: 5,294,615
[45] Date of Patent: Mar. 15, 1994

[54] TERAZOSIN POLYMORPH AND PHARMACEUTICAL COMPOSITION

[75] Inventors: Glenn A. Meyer, Waukegan; John F. Bauer, Lake Bluff, both of Ill.

[73] Assignee: Abbott Laboratories, Abbott Park, Ill.

[21] Appl. No.: 90,721

[22] Filed: Jul. 13, 1993

Related U.S. Application Data

[63] Continuation-in-part of Ser. No. 54,917, Apr. 29, 1993, abandoned.

[51] Int. Cl.$^5$ ............... A61K 31/505; C07D 405/14
[52] U.S. Cl. ................................. 514/254; 544/291
[58] Field of Search ............ 544/291; 514/254; A61K 31/505

[56] References Cited

U.S. PATENT DOCUMENTS

| | | | |
|---|---|---|---|
| 4,026,894 | 5/1977 | Winn et al. | 260/256.4 |
| 4,112,097 | 9/1978 | Winn et al. | 424/251 |
| 4,251,532 | 2/1981 | Roteman | 424/251 |
| 5,122,514 | 6/1992 | Boger et al. | 514/19 |
| 5,212,176 | 5/1993 | Kyncl et al. | 514/254 |

OTHER PUBLICATIONS

Yacobi et al, J. Clin. Pharmacol. 21:301-310 (1981).
Tkaker et al, Am. J. Clin. Nuta. 45(6) 1987.
Serajuddin et al, J. Pharm. Sci. 75(1).1986.62-64.
Yakahe Hakhoechi, 22(1), 49-54 (1992).

*Primary Examiner*—Cecilia Tsang
*Attorney, Agent, or Firm*—Jerry F. Janssen

[57] ABSTRACT

A novel anhydrous crystalline polymorph of 1-(4-amino-6,7-dimethoxy-2-quinazolinyl)-4-(2-tetrahydrofuroyl)piperazine monohydrochloride is disclosed, together with pharmaceutical formulations containing the compound. The novel polymorph exhibits a diminished food effect when administered to human subjects.

8 Claims, 14 Drawing Sheets

TERAZOSIN POLYMORPH AND PHARMACEUTICAL COMPOSITION

CROSS-REFERENCE TO RELATED APPLICATIONS

This application is a continuation-in-part of copending application Ser. No. 08/054,917 filed Apr. 29, 1993, now abandoned.

TECHNICAL FIELD

This invention relates to an organic compound having pharmaceutical utility and to pharmaceutical formulations and their use in the treatment of disease conditions. More particularly, the present invention concerns a novel crystalline polymorph of 1-(4-amino-6,7-dimethoxy-2-quinazolinyl)-4-(2-tetrahydrofuroyl)piperazine monohydrochloride ("terazosin" hydrochloride) and to a soft elastic gelatin capsule formulation comprising terazosin hydrochloride and its use in the treatment of hypertension, benign prostatic hyperplasia, and congestive heart failure.

BACKGROUND OF THE INVENTION

The compound 1-(4-amino-6,7-dimethoxy-2-quinazolinyl)-4-(2-tetrahydrofuroyl)piperazine is known by the common name "terazosin" and is the subject of U.S. Pat. No. 4,026,894. The compound is known to have utility for the treatment of hypertension and benign prostatic hyperplasia, and pharmaceutical compositions comprising terazosin and its salts are claimed in U.S. Pat. No. 4,112,097. The dihydrate crystalline form of the hydrochloride salt of terazosin is disclosed and claimed in U.S. Pat. No. 4,251,532, and is marketed under the trade name Hytrin®. The R(+)-enantiomer of terazosin is disclosed and claimed in U.S. Pat. No. 5,212,176.

SUMMARY OF THE INVENTION

The present invention provides, in its principle embodiment, a new crystalline polymorph of terazosin which possesses unexpectedly uniform bioavailability when administered both postprandially or to fasting patients. The crystalline polymorph of 1-(4-amino-6,7-dimethoxy-2-quinazolinyl)-4-(2-tetrahydrofuroyl)piperazine monohydrochloride of the present invention is characterized by the powder X-ray diffraction pattern, $^{13}C$ nuclear magnetic resonance spectrum, infrared spectrum, and differential scanning calorimetric thermogram of FIGS. 3, 6, 9, and 12 respectively.

In another embodiment of the present invention, there are provided pharmaceutical compositions comprising a therapeutically effective amount of the novel crystalline polymorph described above in combination with a pharmaceutically acceptable carrier.

In yet another embodiment of this invention, there is provided a method of treating hypertension, benign prostatic hyperplasia (BPH), and congestive heart failure comprising administering to a host mammal in need of such treatment a therapeutically effective amount of the crystalline polymorph of terazosin monohydrochloride as described above.

DETAILED DESCRIPTION

Terazosin monohydrochloride, is known to exist in both an anhydrous or anhydrate crystalline form and a dihydrate crystalline form. The dihydrate form, disclosed in U.S. Pat. No. 4,251,532, is characterized by the data shown in FIGS. 2, 5, 8, and 11. When the dihydrate form is dried by conventional methods such as oven drying, the known anhydrate crystalline form, characterized by the data which are presented in FIGS. 1, 4, 7, and 10, is produced. However, in accordance with the present invention, it has been unexpectedly found that when the previously known dihydrate crystalline form of terazosin is dried by being first dissolved in a dry, polar organic solvent such as acetone, methanol, ethanol, polyethylene glycol, or similar dry, polar solvent and subsequently precipitated, they are converted to the novel polymorph of the present invention which is characterized by the powder X-ray diffraction pattern, $^{13}C$ nuclear magnetic resonance spectrum, infrared spectrum, and differential scanning calorimetric thermogram of FIGS. 3, 6, 9, and 12, respectively.

Comparison of the data from these Figures with the corresponding data for the anhydrous crystalline form (FIGS. 1, 4, 7, and 10) and the dihydrate crystalline form (FIGS. 2, 5, 8, and 11) shows clearly that the material of the present invention is a different crystalline form from either of the previously known forms. For example, in addition to differences in the powder X-ray diffraction patterns between the prior art forms of terazosin monohydrochloride and that of the present invention, there are also observable differences in the solid state $^{13}C$ nuclear magnetic resonance spectra appearing in FIGS. 4 (prior art anhydrate), 5 (prior art dihydrate) and 6 (new modification according to the present invention) and the differential scanning calorimetric thermograms appearing in FIGS. 10 (prior art anhydrate), 11 (prior art dihydrate) and 12 (new modification according to the present invention). For example, the thermograms of both the anhydrate (FIG. 10) and the dihydrate (FIG. 11) show a sharp endotherm beginning at about 260° C., characteristic of melting, while for the dihydrate there is a broad endotherm beginning at a lower temperature corresponding to dehydration. In the thermogram of the material of the present invention, the endotherm attributed to dehydration is missing and melting begins at about 250° C.

The powder X-ray crystallographic data, considered together with the solid state $^{13}$C NMR and infrared spectra data and the scanning differential calorimetric thermograms clearly indicate that the material of the present invention is a different crystalline form of 1-(4-amino-6,7-dimethoxy-2-quinazolinyl)-4-(2-tetrahydrofuroyl)piperazine monohydrochloride from either the prior art anhydrate or the prior art dihydrate.

The novel anhydrous crystalline polymorph of the present invention is readily prepared by dissolving either the known monohydrochloride dihydrate or the known monohydrochloride anhydrate crystalline form of 1-(4-amino-6,7-dimethoxy-2-quinazolinyl)-4-(2-tetrahydro-furoyl)piperazine in a first dry, polar organic solvent to produce a clear solution, followed by precipitation of the dissolved solids by addition of a second dry polar organic solvent which is miscible in the first, but which is of a lower polarity than the first.

The solvents employed for this process are selected from acetone and alcohols such as methanol, ethanol, propanol, isopropanol or any of the polyethylene glycols, commonly known as "PEG's" of average molecular weights ranging between about 200 and 600 Daltons. The preferred first solvent is methanol and the preferred second solvent is acetone. The solvents are carefully dried prior to use by methods well known in the art such as contacting them with dehydrating aluminosilicate or aluminophosphate zeolites, commonly called "molecular sieves." The molecular sieves are chosen from those grades having a pore size which is optimized for trapping water molecules, preferably about 4 Ångstrom units. The solvent is allowed to stand at room temperature over the molecular sieves until dry, generally for a period of from about 24 to about 48 hours. An additional drying step may be taken which consists of contacting the molecular sieve-dried solvent with anhydrous magnesium or sodium sulfate or of filtering the molecular sieve-dried solvent through a pad of anhydrous magnesium or sodium sulfate prior to use. The water content of the solvents can be checked by well known methods such as the Karl Fischer method (*Angew. Chem.*, 48:394 (1935); D. Smith, et al., *J. Am. Chem. Soc.*, 61:2407 (1939)).

In a preferred method of this invention, 1-(4-amino-6,7-dimethoxy-2-quinazolinyl)-4-(2-tetrahydro-furoyl)-piperazine monohydrochloride dihydrate, prepared as described in U.S. Pat. No. 4,251,532, is dissolved in previously dried methanol, in a volume sufficient to produce a clear solution. If the solution has a slight cloudiness, more methanol may be added to the point of clarity or the solution may be filtered. Carefully dried acetone is then added to the methanol solution until a slight haze develops in the solution. The resulting mixture is then allowed to stand, and may be optionally cooled, until precipitation is complete. The precipitated solid is collected by filtration. Material prepared in this manner is typically completely converted to the novel anhydrous crystalline polymorph of the present invention and is free of detectable traces of other crystalline forms of terazosin monohydrochloride.

Also contemplated as falling within the scope of the present invention are pharmaceutical formulations comprising a therapeutically effective amount of the novel crystalline polymorph of terazosin monohydrochloride of this invention in combination with a suitable pharmaceutically acceptable carrier. A preferred formulation in accordance with the invention comprises a unit dosage form comprising an outer soft elastic gelatin shell, and an inner composition filling said shell comprising a) an active drug component comprising a crystalline polymorph of 1-(4-amino-6,7-dimethoxy-2-quinazolinyl)-4-(2-tetrahydrofuroyl)piperazine monohydrochloride characterized by the powder X-ray diffraction pattern, $^{13}$C nuclear magnetic resonance spectrum, infrared spectrum, and differential scanning calorimetric thermogram of FIGS. 3, 6, 9, and 12 show, respectively and b) a pharmaceutically acceptable non-aqueous liquid carrier. A particularly preferred non-aqueous liquid carrier is poly(ethylene glycol).

The preferred pharmaceutical compositions of the present invention comprise a dosage form of terazosin hydrochloride in which the active drug component is dissolved or suspended in a liquid, non-aqueous pharmaceutical carrier encapsulated within a soft elastic capsule (SEC) shell.

The outer soft elastic shell of the formulations of this invention comprises gelatin which is plasticised by the addition of glycerin, sorbitol or other polyol. The preferred capsule composition of the formulations of this invention comprises primarily a gelatin/glycerin mixture ranging between about 50 weight percent gelatin to about 60 weight percent gelatin, with about 55 to 58 weight percent gelatin being preferred. Small amounts of antimicrobial or antifungal agents such as methylparaben, propylparaben and mixtures of the alkylparabens are also present in amounts ranging between about 0.25 weight percent to about 0.4 weight percent, preferably about 0.3 weight percent of the total soft gelatin capsule shell weight. Flavoring agents are optionally added to the soft elastic gelatin capsule formula in amounts ranging between about 0.25 weight percent to about 0.4 weight percent, preferably about 0.3 weight percent of the total soft gelatin capsule shell weight to provide a pleasant taste to the capsule formulation. A preferred flavoring agent for formulations in accordance with the present invention is ethyl vanillin.

Opacifying or coloring agents such as titanium dioxide or iron oxide are also optionally added in amounts ranging between about 0.25 weight percent to about 0.5 weight percent, preferably about 0.3 weight percent of the total soft gelatin capsule shell weight to provide the desired color or opacity to the soft gelatin shell. When white titanium dioxide is used as the opacifying agent, various pharmaceutically acceptable dyes such as FD&C Blue, D&C Yellow, and FD&C Red may also be added to obtain the desired final color of the gelatin shell for identification purposes.

The inner fill composition of the formulations of the present invention comprises from between 1 and 15 mg of 1-(4-amino-6,7-dimethoxy-2-quinazolinyl)-4-(2-tetrahydrofuroyl)piperazine or a pharmaceutically acceptable salt thereof, with the hydrochloride salt being particularly preferred. The active drug component is dissolved and/or suspended in an inert, non-aqueous, pharmaceutically acceptable liquid carrier. Preferred carriers are selected from the polyethylene glycols, known in the trade as "PEG's," particularly PEG's having an average molecular weight in the range between about 200 and 600, with PEG 400 being most preferred. The liquid fill comprises from about 80–300 mg of PEG with the typical amount of PEG ranging between about 90–110 mg. The carrier may also include viscosity-building agents such as polyvinylpyrrolidone or silica gel and agents which enhance the suspendability of the drug component in the liquid carrier. Small amounts of glycerin, ranging between about 1–4 weight percent, preferably about 1.5–2 weight percent, based upon the total weight of the fill composition, may also be added to the liquid carrier to retard the migration of glycerin out of the soft elastic gelatin capsule shell into the inner liquid fill.

The SEC formulations of the present invention are generally prepared by methods well known in the formulation arts. See, for example "Remington's Pharmaceutical Sciences," 18th Edition, A. Gennaro, Ed., Mack Publishing Co., Easton, Pa., 1990, pp. 1662–1663. The capsules may be made by the so-called "plate process" in which a warm sheet of plasticized gelatin is placed on one of two molds containing depressions into which the drug fill is placed. A second sheet of warm gelatin and the second half of the mold is placed over the first and the sandwich pressed to form the soft elastic capsules. This technique permits the formation of soft elastic capsules in which the two halves of the capsule may be of different color for identification purposes.

In the so-called rotary-die process, two ribbons of gelatin are fed continuously into a rotating die assembly which converge adjacent to a fill-injector. The two gelatin ribbons are simultaneously formed into the two halves of the capsule which are filled and subsequently sealed as the die assembly rotates. The fill-injector is actuated by a pump which measures and dispenses the appropriate volume (dose) of the active drug component. This process permits accurate and reproducible formulations.

When formulated into the referred SEC pharmaceutical dosage form and administered to healthy human subjects, the new crystalline polymorph of terazosin monohydrochloride of this invention exhibits an observably diminished "food effect" when compared with dosage forms comprising the prior art dihydrate form. By the term "food effect" is meant differences between the times required to reach peak blood serum concentrations and the peak serum concentrations of the drug following administration to a fasting patient as opposed to administration postprandially.

The novel crystalline polymorph of terazosin monohydrochloride of the present invention was administered to 35 healthy human subjects in a soft elastic gelatin capsule dosage form. A significantly lower "food effect" was observed with the administration of this crystalline modification when compared with similar administration of the prior art tablet form of 1-(4-amino-6,7-dimethoxy-2-quinazolinyl)-4-(2-tetrahydrofuroyl)-piperazine monohydrochloride dihydrate. In each case, 2 mg of terazosin was administered to subjects thirty minutes after eating and to the subjects in the fasting state. The serum levels of terazosin were measured, together with the maximum serum concentration ($C_{max}$) and the time required to reach maximum serum concentration ($t_{max}$). The results appear in Table 1.

TABLE 1

Effect of Food on Bioavailability of Terazosin Administered in the Tablet vs. Soft Gelatin Capsule Formulation

| Para- | SEC Formulation | | Prior Art Formulation | |
|---|---|---|---|---|
| meter | Fasting | Postprandial | Fasting | Postprandial |
| $C_{max}$ ($\mu$M) | 40.70 ± 9.4 | 43.33 ± 8.8 | 41.85 ± 22.39 | 31.01 ± 11.27 |
| $t_{max}$ (Hrs.) | 1.2 | 1.9 | 1.3 | 2.4 |

The data in Table 1 show that there is only a small difference in the maximum serum concentration of 1-(4-amino-6,7-dimethoxy-2-quinazolinyl)-4-(2-tetrahydrofuroyl)-piperazine monohydrochloride administered either to a fasting patient or postprandially by means of the SEC formulation. Moreover, there is only a 0.7 hour difference in the time required to reach maximum serum concentration of terazosin administered by means of the SEC formulation of the present invention.

However, when terazosin monohydrochloride dihydrate is administered by means of the prior art tablet formulation, there is an observable difference in the maximum serum concentration when administered postprandially versus administration to a fasting patient. In this case, under the test conditions, there is also an approximate doubling of the time required for the postprandial dose of terazosin to reach maximum serum concentration.

Figure 1:
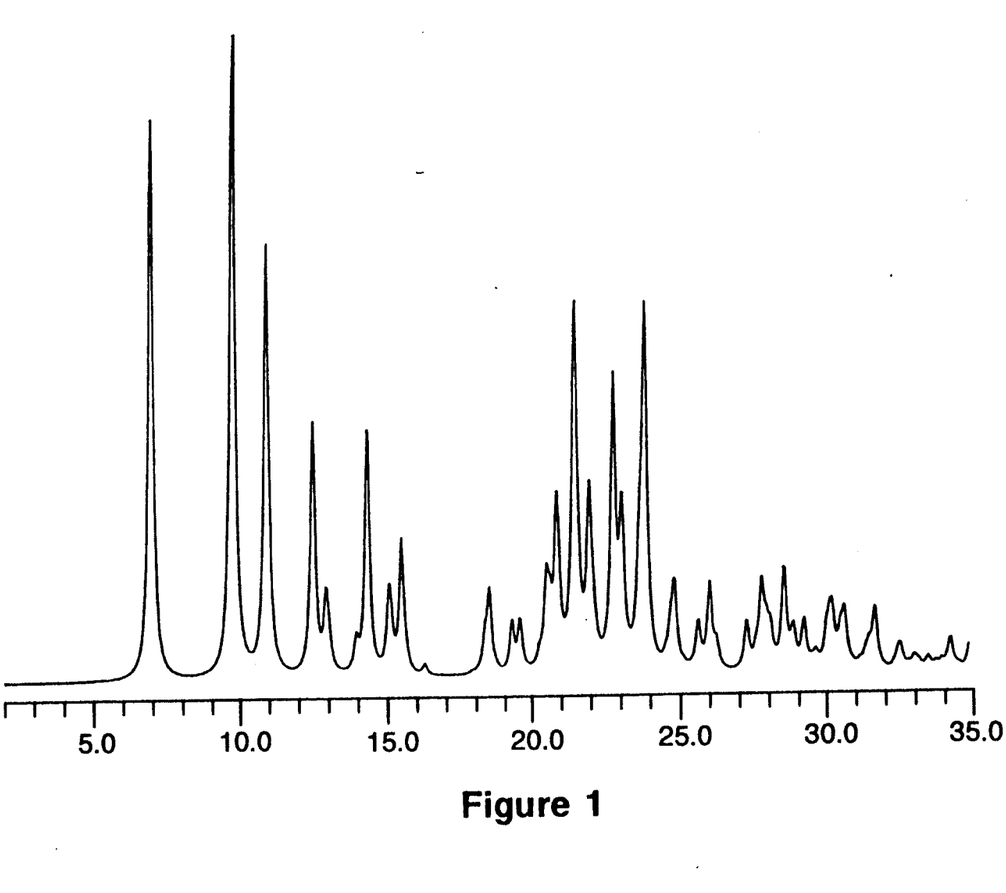
FIGS. 1, 4, 7, and 10 show, respectively, the powder X-ray diffraction pattern, the $^{13}C$ nuclear magnetic resonance spectrum, the infrared spectrum, and the differential scanning calorimetric thermogram of the prior art anhydrate form of 1-(4-amino-6,7-dimethoxy-2-quinazolinyl)-4-(2-tetrahydrofuroyl)piperazine monohydrochloride.
Figure 2:
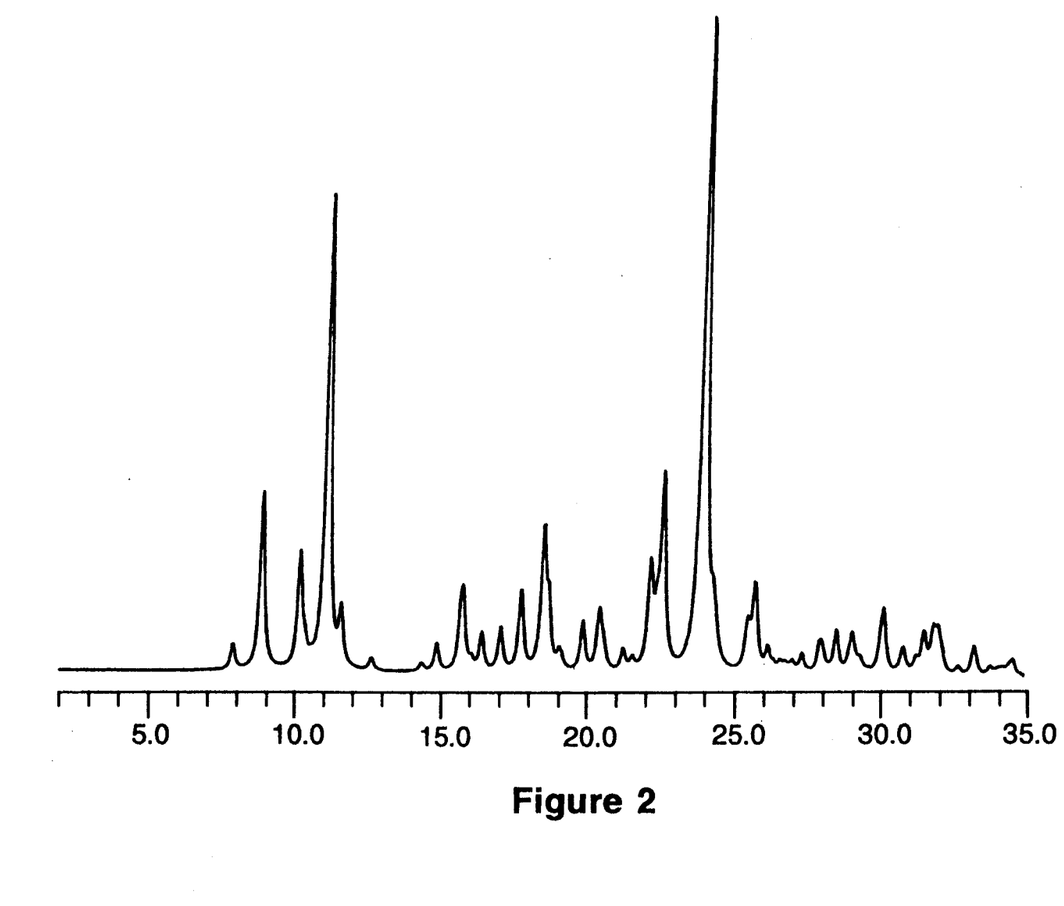
FIGS. 2, 5, 8, and 11 show, respectively, the powder X-ray diffraction pattern, the $^{13}C$ nuclear magnetic resonance spectrum, the infrared spectrum, and the differential scanning calorimetric thermogram of the prior art dihydrate form of 1-(4-amino-6,7-dimethoxy-2-quinazolinyl)-4-(2-tetrahydrofuroyl)piperazine monohydrochloride.
Figure 3:
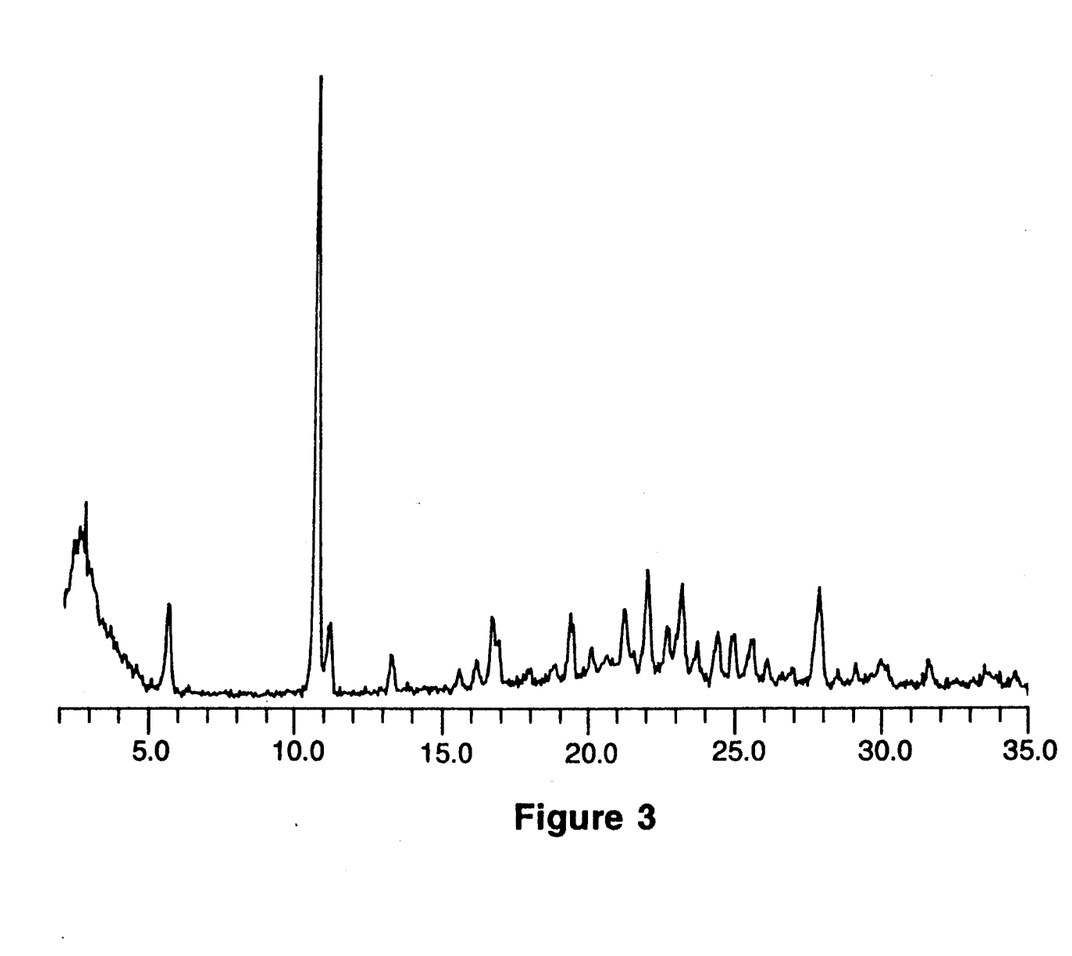
FIGS. 3, 6, 9, and 12 show, respectively, the powder X-ray diffraction pattern, the $^{13}C$ nuclear magnetic resonance spectrum, the infrared spectrum, and the differential scanning calorimetric thermogram of the form of 1-(4-amino-6,7-dimethoxy-2-quinazolinyl)-4-(2-tetrahydrofuroyl)piperazine monohydrochloride of the present invention.
Figure 4:
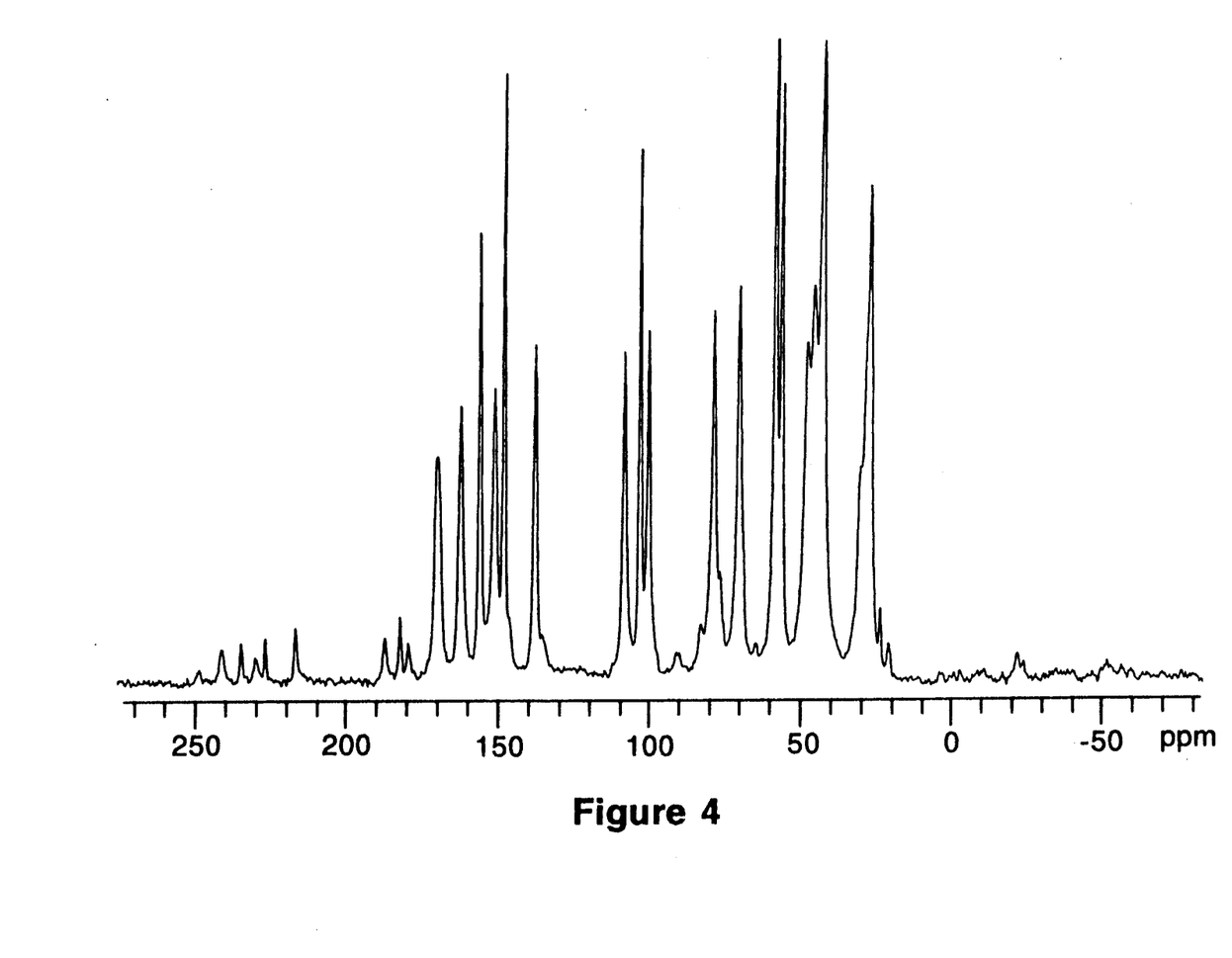
Figure 5:
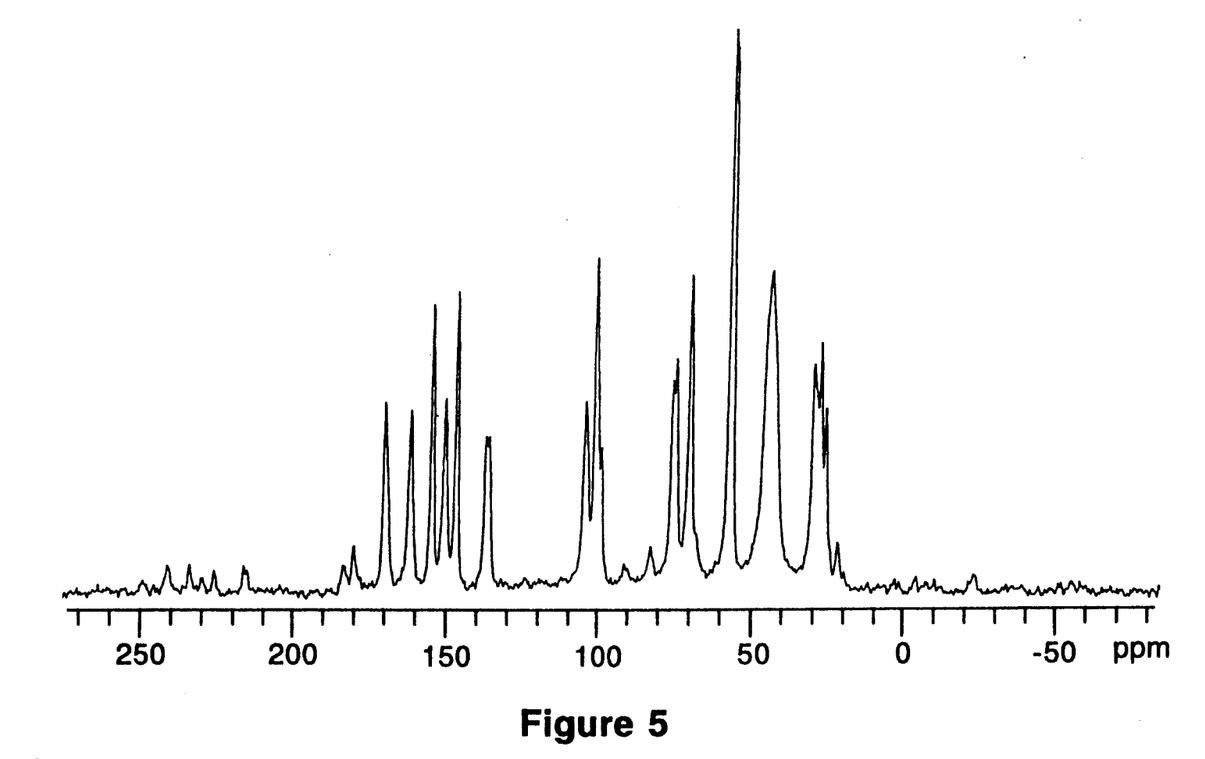
Figure 6:
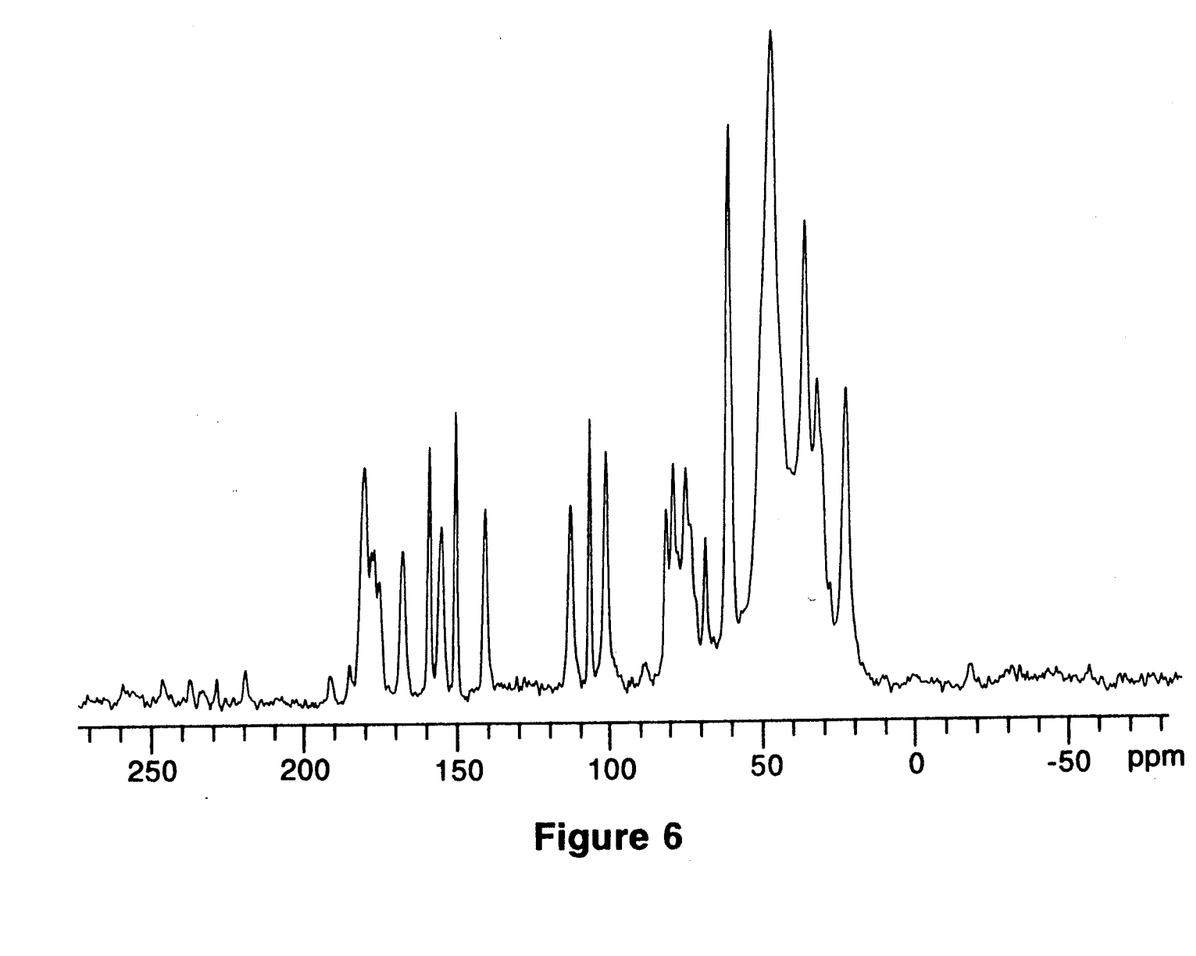
Figure 7:
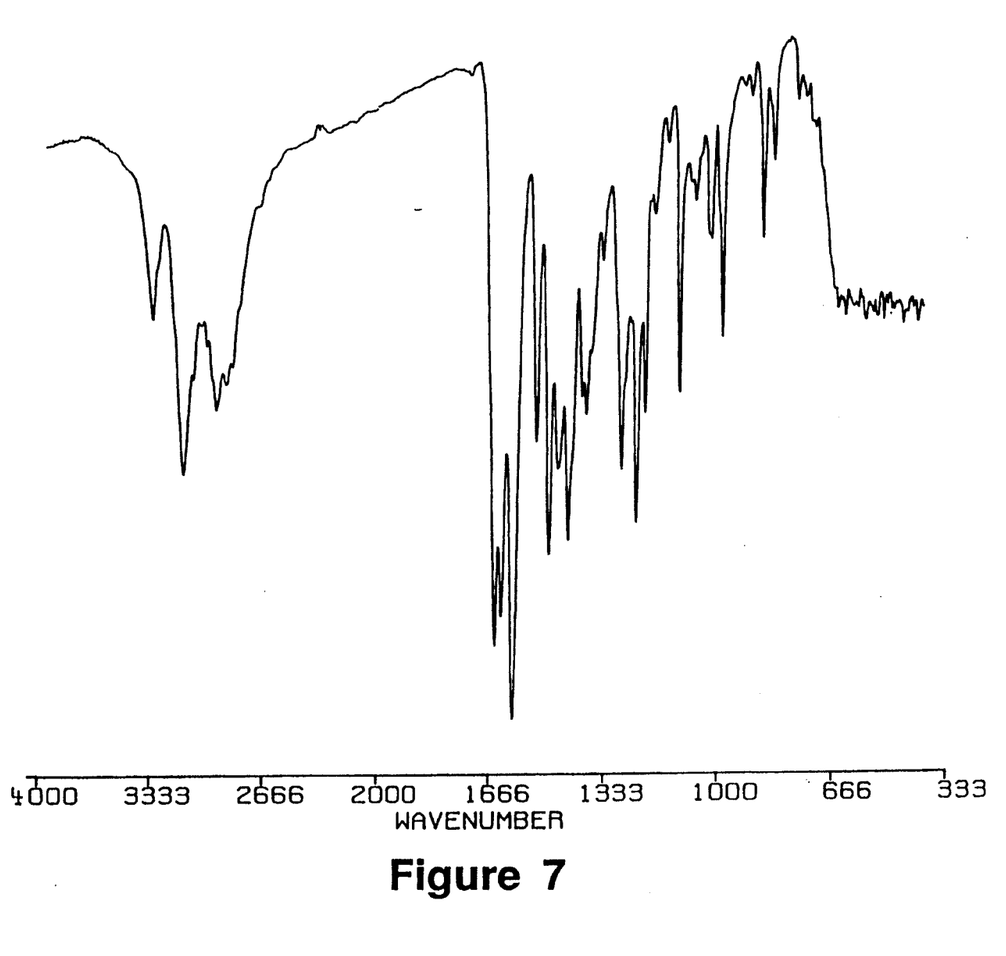
Figure 8:
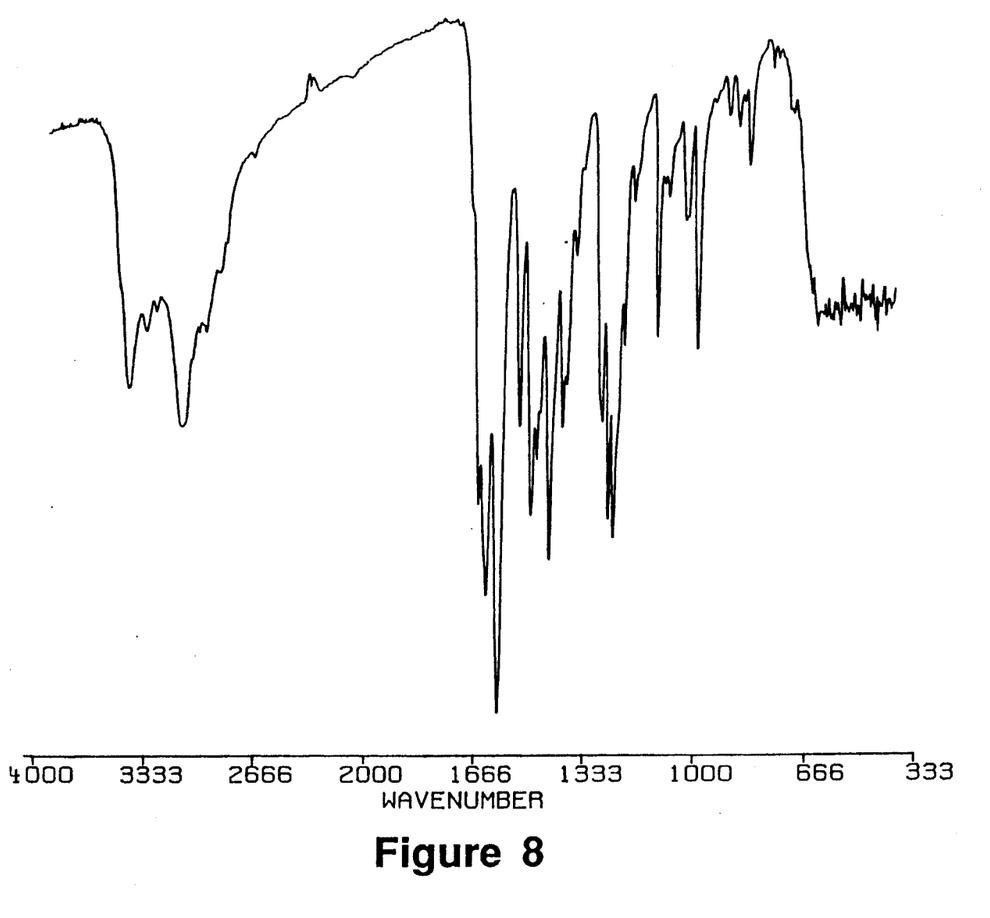
Figure 9:
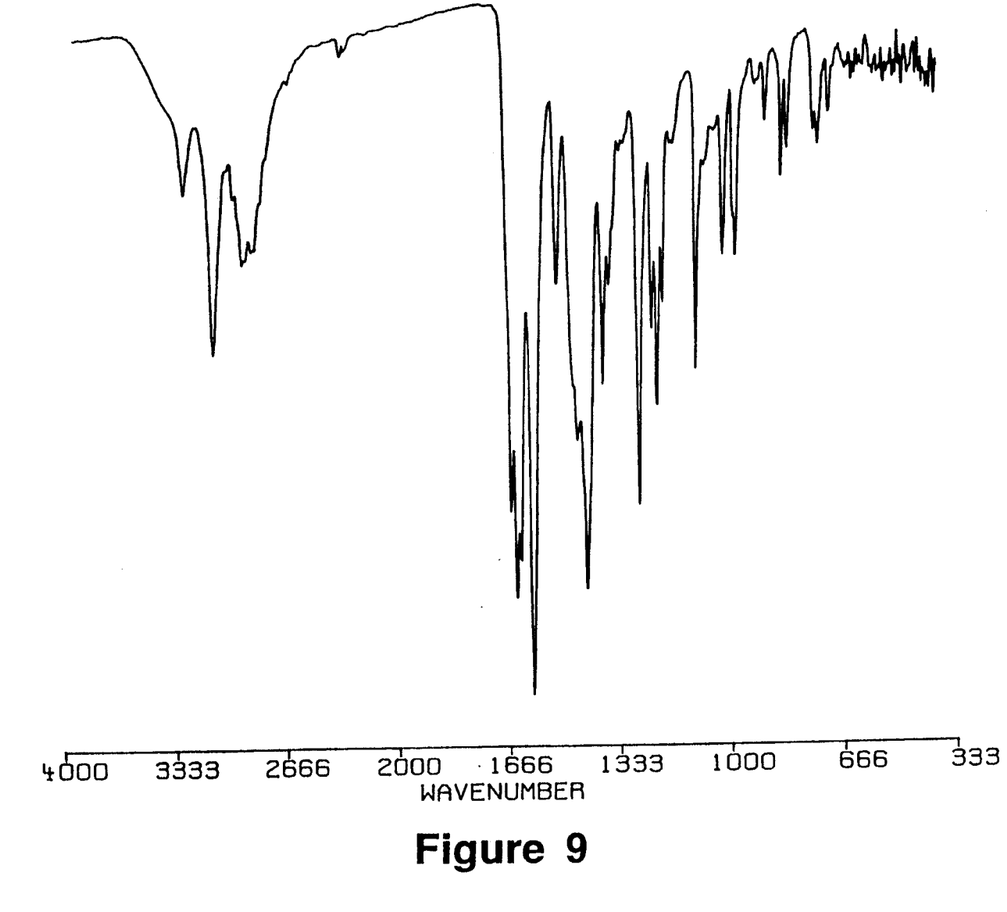
Figure 10:
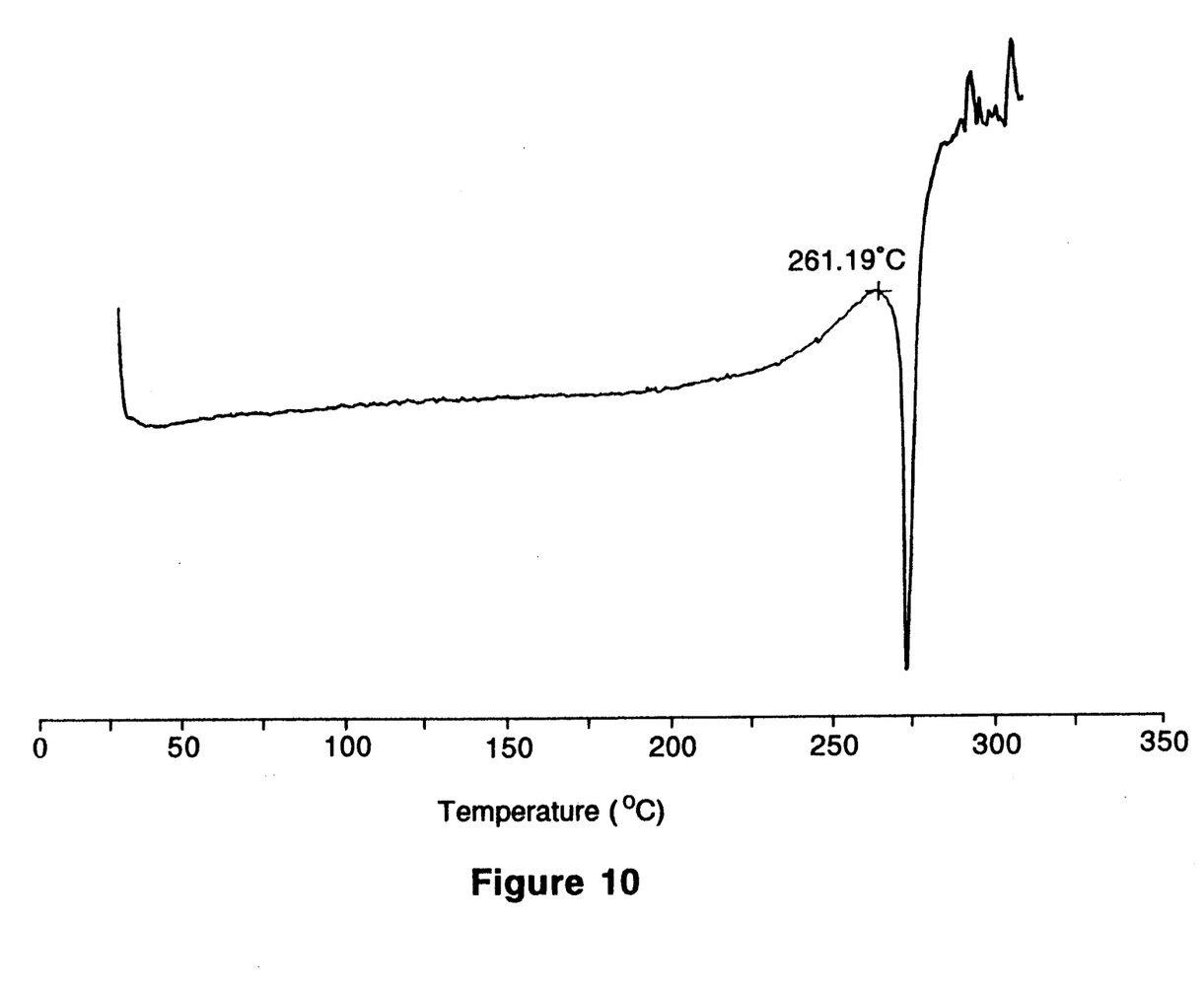
Figure 11:
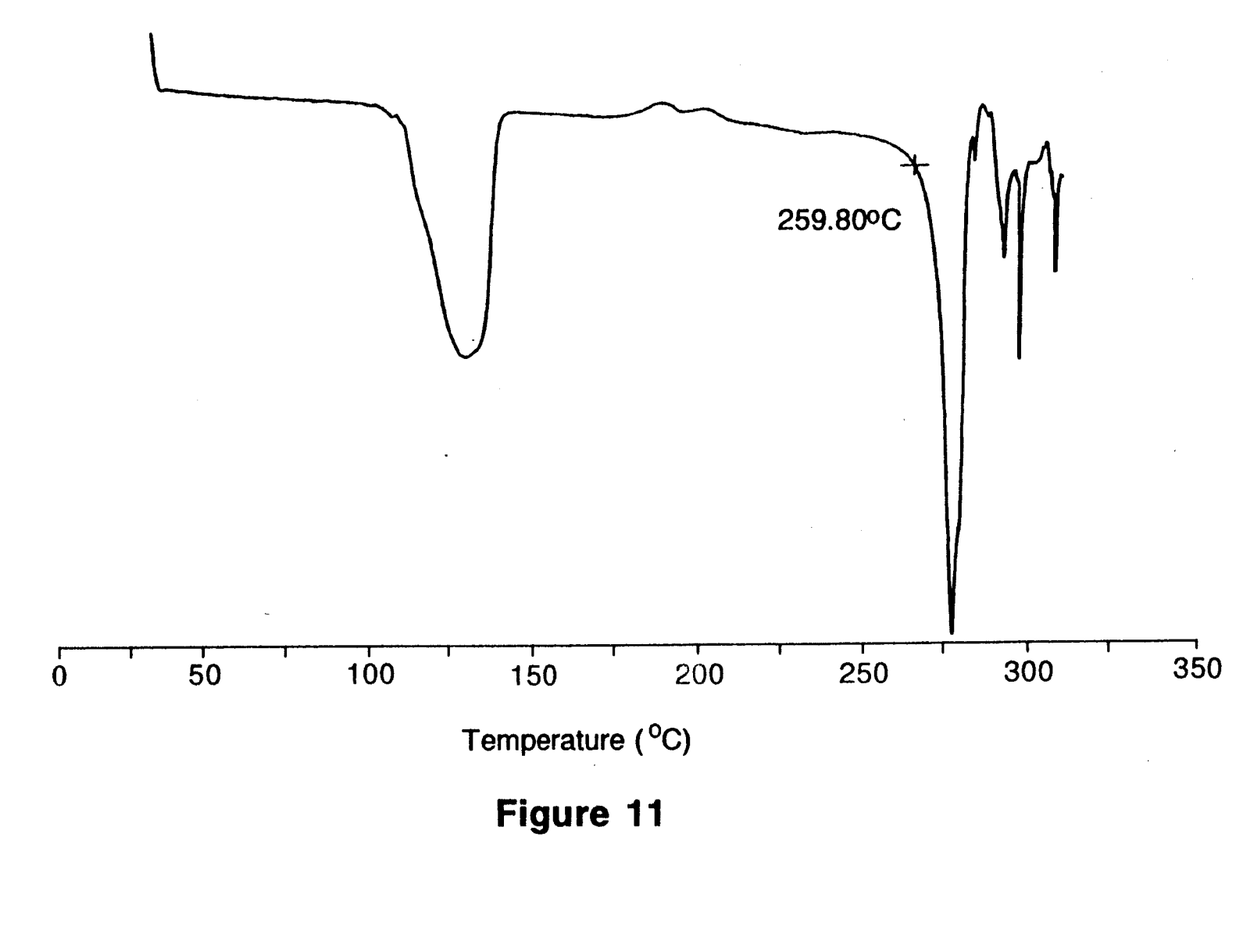
Figure 12:
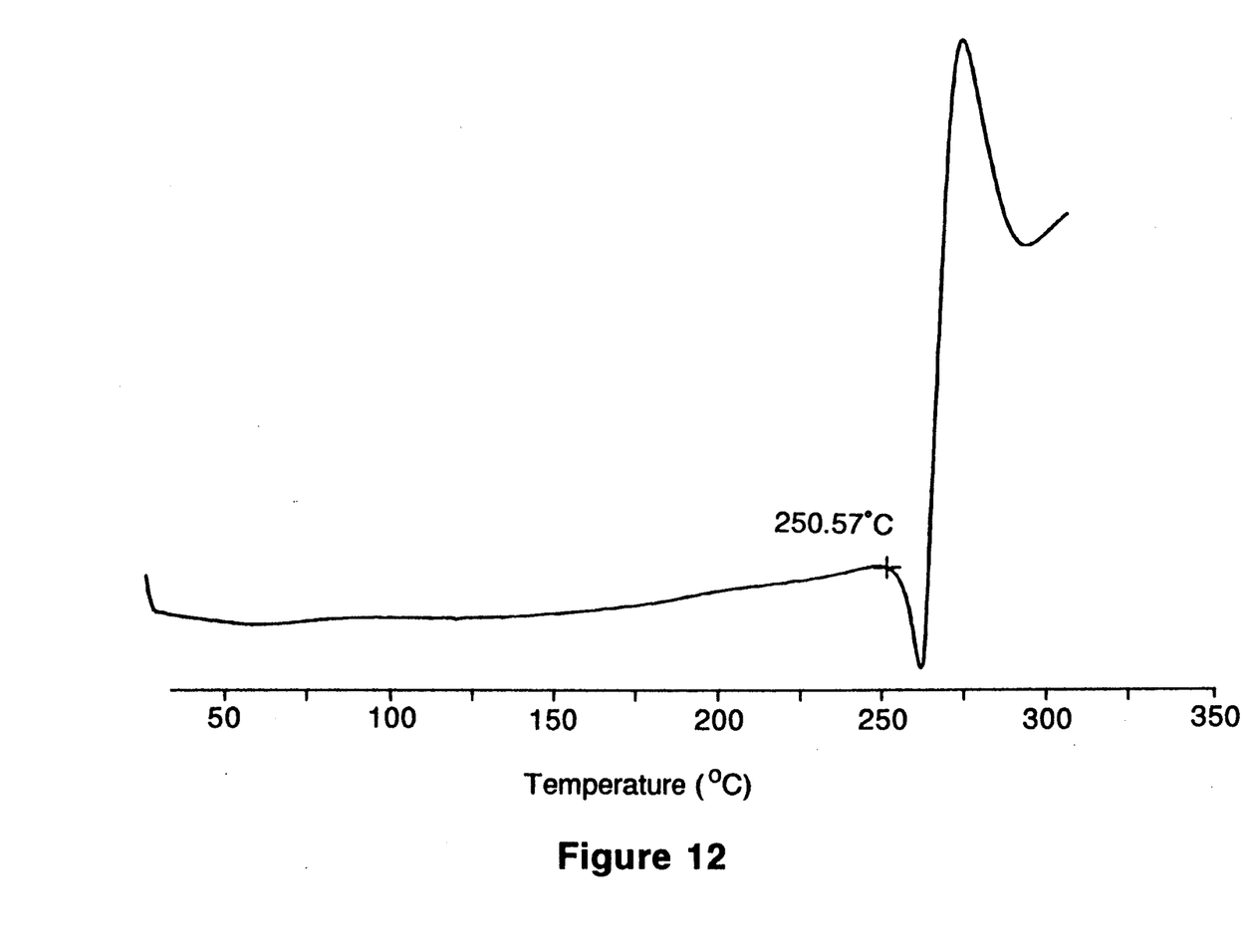
Figure 13:
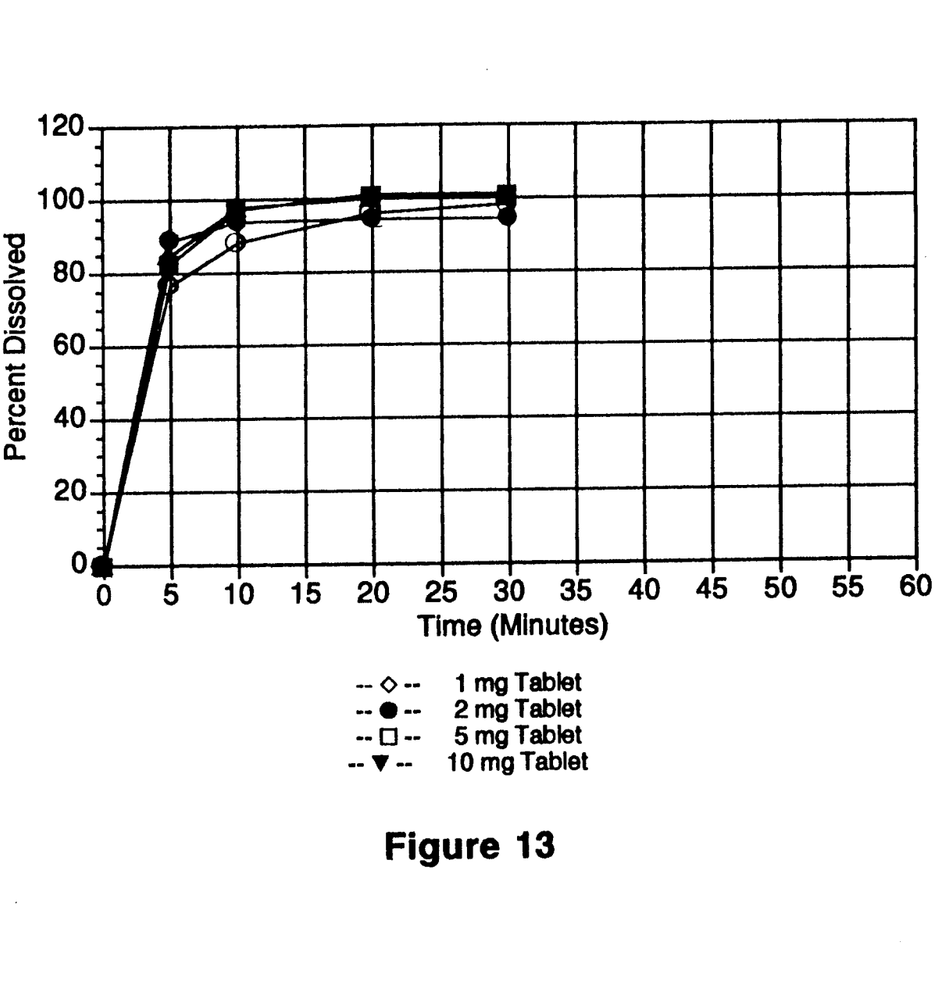
FIG. 13 shows the rates of dissolution in water at 37° C. of the prior art hydrochloride dihydrate form of 1-(4-amino-6,7-dimethoxy-2-quinazolinyl)-4-(2-tetrahydrofuroyl)piperazine monohydrochloride in 1, 2, 5, and 10 mg tablet formulations.
Figure 14:
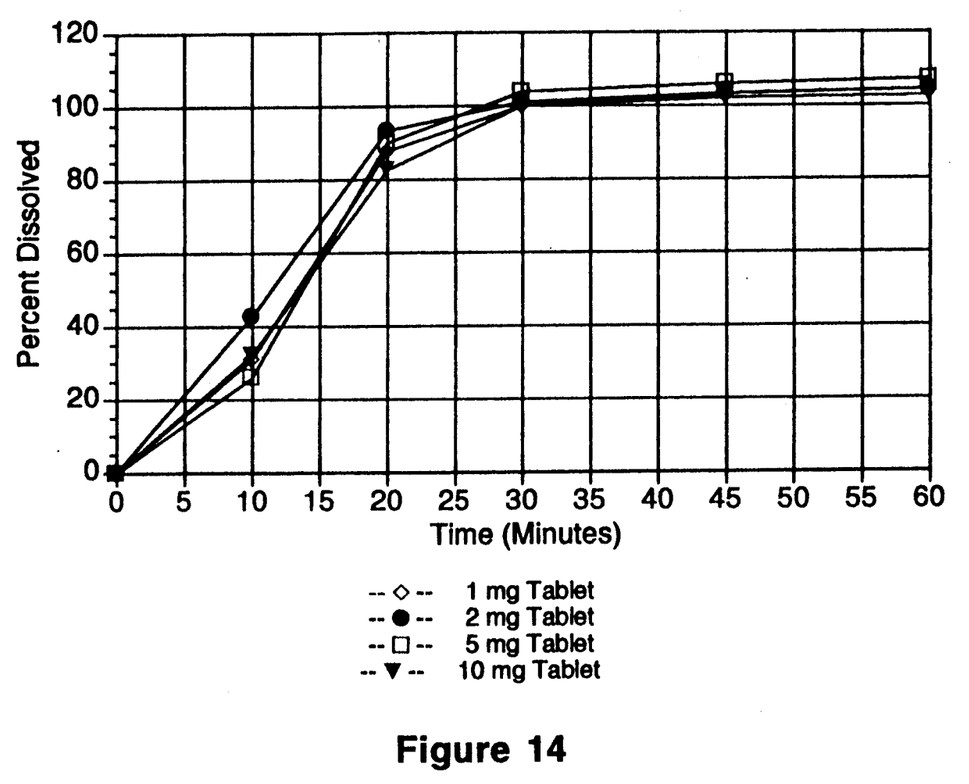
FIG. 14 shows the rates of dissolution of 1-(4-amino-6,7-dimethoxy-2-quinazolinyl)-4-(2-tetrahydrofuroyl)piperazine monohydrochloride in 1, 2, 5, and 10 mg soft elastic gelatin capsule (SEC) formulations in accordance with the present invention.

This "food effect" difference between the prior art tablet formulation for terazosin and the SEC formulation is surprising and appears not to be simply the result of the difference in the dosage forms. As shown by the data in FIGS. 13 and 14, the tablet form is observed to dissolve more rapidly than the SEC formulation. The rates of solubility in water of various dosages of the prior art tablet formulation and the SEC formulation of the present invention were measured by standard methods. In FIG. 13 there are shown graphically the rates of solubility of various doses of the prior art dihydrate crystalline form of terazosin monohydrochloride and in FIG. 14 there are shown graphically the rates of solubility of similar doses of a soft elastic gelatin capsule (SEC) formulation terazosin monohydrochloride dihydrate. As can be seen by comparing the two Figures, all doses of the prior art tablet form are essentially completely dissolved after 15 minutes. Under similar conditions, complete solubility of the SEC formulation of the present invention is achieved for the various doses only after about 30 minutes.

The lower standard deviation relative to the mean for the soft gelatin capsule formulation compared with that of the prior art tablet form for administration to patients both postprandially and in the fasting state supports these conclusions.

The present invention also includes the use of the novel crystalline polymorph of terazosin monohydrochloride in the treatment of hypertension, congestive heart failure, and benign prostatic hyperplasia. In these uses, the compound is administered to subjects in need of such treatment in amounts ranging between about 0.5 mg to about 20 mg, preferably in the range of between about 1 mg and 10 mg per day, and most preferably in the range of about 1 mg to 5 mg per day. The actual dose administered in a particular case will depend upon the weight and physical condition of the patient and the severity of the disease condition. However, it is well within the skill of the physician to begin administration with a low dose and gradually increase the dose until the desired therapeutic effect is achieved.

The following examples are provided to enable one skilled in the art to practice the present invention, but should not be read as limiting the scope of the invention as it is defined by the appended claims.

EXAMPLE 1

Preparation of the Anhydrous Crystalline Polymorph of Terazosin Monohydrochloride-Suspension Method Acetone was carefully dried for 48 hours at room temperature over molecular sieves (4 Ångstorm pore size) which had been previously dried at 190° C. The acetone was then decanted and further dried by contacting with anhydrous sodium sulfate for an additional 12 hours. Alternatively, the acetone may be decanted from the molecular sieves and filtered through a pad of anhydrous sodium sulfate.

Terazosin dihydrate monohydrochloride (1 g) was suspended in 10 ml of this previously dried acetone and the mixture thoroughly shaken and then allowed to stand for a period of 48 hours. At the end of this time the solid was collected by filtration and air dried. The material was analyzed by X-ray powder diffraction and shown to comprise approximately 45% of the new crystalline polymorph.

EXAMPLE 2

Preparation of the Anhydrous Crystalline Polymorph of Terazosin Monohydrochloride-Solution Method Dry acetone and dry methanol were separately prepared by drying for 48 hours at room temperature by the method detailed in Example 1 above.

Terazosin monohydrochloride dihydrate (3 gm, 6.5 mmol) was stirred in 100 mL of the dried methanol at ambient temperature until a clear solution was obtained. The previously dried acetone was carefully added to the resulting solution until a slight haze developed in the mixture. The mixture was allowed to stand until the terazosin hydrochloride precipitated. Solid anhydrous terazosin monohydrochloride (2.5 g, 5.9 mmol, 90% yield) was obtained. Thermogravimetric analysis indicated that the material did not contain any water or other solvent of crystallization. The powder X-ray diffraction pattern of the material indicated that it was free of detectable amounts of either the dihydrate starting material or the prior art anhydrate crystalline form.

EXAMPLE 3

Preparation of Inner Fill Composition 1-(4-Amino-6,7-dimethoxy-2-quinazolinyl)-4-(2-tetrahydrofuroyl)piperazine monohydrochloride dihydrate is sieved through a 40 mesh screen to remove any aggregated material.

Glycerin (2-4 parts by weight) is dispersed in about 95 parts by weight PEG 400 and stirred with sparging by dry nitrogen until a uniform mixture is obtained. Polyvinylpyrrolidone (5 parts by weight) is added to the PEG 400/glycerin mixture and stirred until completely dissolved. 1-(4-Amino-6,7-dimethoxy-2-quinazolinyl)4-(2-tetrahydrofuroyl)-piperazine monohydrochloride dihydrate (1-20 parts by weight) is added to the PEG 400/glycerin/polyvinylpyrrolidone mixture and stirred until a uniform mixture is obtained. The resulting mixture is passed through a mill to deagglomerate solids.

EXAMPLE 4

Preparation of the Soft Elastic Capsule Shell Composition

Gelatin (50.94 parts by weight) is melted and blended with glycerin (38.57 parts by weight) to obtain a uniform mixture. Methylparaben (0.2128 parts by weight) and propylparaben (0.0532 parts by weight) are added to the gelatin/glycerin mixture and stirred to obtain a uniform mixture. Ethyl vanillin (0.2660 parts by weight), titanium dioxide (0.2926 parts by weight), and FD&C Blue No. 1 (0.0335 parts by weight) are added to the mixture and stirred to obtain a uniform mixture.

The final mixture is formed into sheets, allowed to harden, and cut into strips for use in the SEC encapsulating machine.

EXAMPLE 5

Soft Elastic Gelatin Capsule Production

Using an SEC encapsulating machine, soft elastic gelatin capsules comprising an inner fill of 10 mg of 1-(4-amino-6,7-dimethoxy-2-quinazolinyl)-4-(2-tetrahydrofuroyl)-piperazine monohydrochloride, 5 mg of polyvinylpyrrolidone, 2.12 mg of glycerine and 94.98 mg of PEG 400 were prepared.

While there have been shown and described what are believed at the present time to be the preferred embodiments of the present invention, it will be evident to one of ordinary skill in the art that various modifications may be made without departing from the scope of the invention as it is defined by the appended claims.

We claim:

1. A crystalline polymorph of 1-(4-amino-6,7-dimethoxy-2-quinazolinyl)-4-(2-tetrahydrofuroyl)piperazine monohydrochloride characterized by peaks in the powder X-ray diffraction pattern at values of 2 theta of 5.5°±0.2°, 10.6°±0.2°, 11.1°±0.2°, 16.7°±0.2°, 19.4°±0.2°, 21.3°±0.2°, 22.0°±0.2°, 22.7°±0.2°, 23.1°±0.2°, 24.4°±0.2°, 24.9°±0.2°, 25.5°±0.2°, and 27.8°±0.2°.

2. A pharmaceutical composition comprising a therapeutically effective amount of a compound as defined by claim 1 in combination with a pharmaceutically acceptable carrier.

3. A pharmaceutical composition as defined by claim 2 in unit dosage form comprising
an outer soft elastic gelatin shell, and
an inner composition filling said shell comprising
  a) an active drug component comprising a crystalline polymorph of 1-(4-amino-6,7-dimethoxy-2-quinazolinyl)-4-(2-tetrahydrofuroyl)piperazine monohydrochloride characterized by principal peaks in the powder X-ray diffraction pattern at values of 2 theta of 5.5°±0.2°, 10.6°±0.2°, 11.1°±0.2°, 16.7°±0.2°, 19.4°±0.2°, 21.3°±0.2°, 22.0°±0.2°, 22.7°±0.2°, 23.1°±0.2°, 24.4°±0.2°, 24.9°±0.2°, 25.5°±0.2°, and 27.8°±0.2°, and
  b) a pharmaceutically acceptable non-aqueous liquid carrier.

4. A pharmaceutical composition as defined by claim 3 wherein said non-aqueous liquid carrier comprises poly(ethylene glycol).

5. A pharmaceutical dosage form as defined by claim 3 wherein said active drug component is present in an amount ranging between 1 mg and 20 mg.

6. A method of treating hypertension comprising administering to a host mammal in need of such treatment a therapeutically effective amount of a pharmaceutical dosage form as defined by claim 3.

7. A method of treating benign prostatic hyperplasia comprising administering to a host mammal in need of such treatment a therapeutically effective amount of a pharmaceutical dosage form as defined by claim 3.

8. A method of treating congestive heart failure comprising administering to a host mammal in need of such treatment a therapeutically effective amount of a pharmaceutical dosage form as defined by claim 3.

* * * * *